United States Patent [19]

Bank et al.

[11] Patent Number: 5,374,757
[45] Date of Patent: Dec. 20, 1994

[54] PROCESS FOR ORGANOOXYLATION OF CYANOALKYLCHLOROSILANES

[75] Inventors: Howard M. Bank, Freeland; Richard D. Meindertsma, Midland, both of Mich.

[73] Assignee: Dow Corning Corporation, Midland, Mich.

[21] Appl. No.: 240,425

[22] Filed: May 10, 1994

[51] Int. Cl.$^5$ .............................. C07F 7/10
[52] U.S. Cl. .................................. 556/415
[58] Field of Search ......................... 556/415

[56] References Cited

U.S. PATENT DOCUMENTS 4,876,337  10/1989  Rauleder et al. ............... 556/415

Primary Examiner—Paul F. Shaver
Attorney, Agent, or Firm—William F. Boley

[57] ABSTRACT

A process for the organooxylation of β-cyanoalkylchlorosilanes. The process comprises contacting in a film a β-cyanoalkylchlorosilane with an alcohol capable of forming an ester with the silicon of the β-cyanoalkylchlorosilane and thereby forming an equilibrium mixture comprising a (β-cyanoalkyl)organooxysilane and hydrogen chloride. The film is heated at a temperature sufficient to cause vaporization of the hydrogen chloride from the equilibrium mixture thereby increasing yield of (β-cyanoalkyl)organooxysilane in the equilibrium mixture. In a preferred process, the process is run in a falling-film type reactor or a wiped-film type reactor.

16 Claims, No Drawings

PROCESS FOR ORGANOOXYLATION OF CYANOALKYLCHLOROSILANES

BACKGROUND OF INVENTION

The present invention is a process for the organooxylation of β-cyanoalkylchlorosilanes. The process comprises contacting in a film a β-cyanoalkylchlorosilane with an alcohol capable of forming an ester with the silicon of the β-cyanoalkylchlorosilane and thereby forming an equilibrium mixture comprising a (β-cyanoalkyl)organooxysilane and hydrogen chloride. The thin film is heated at a temperature sufficient to cause vaporization of the hydrogen chloride from the equilibrium mixture thereby increasing yield of (β-cyanoalkyl)organooxysilane in the equilibrium mixture. In a preferred process, the process is run in a falling-film type reactor or a wiped-film type reactor.

The (β-cyanoalkyl)organooxysilanes prepared by the present process are useful intermediates in the production of other silanes and for the production of polyorganosiloxanes containing the beta-cyanoalkyl substituent. The silicon-bond beta-cyanoalkyl radical is resistant to hydrolysis and can provide a means by which amine containing silanes and siloxanes can be formed.

The reaction of an alcohol with a β-cyanoalkylchlorosilane to form a (β-cyanoalkyl)organooxysilane is an equilibrium reaction exemplified by the following equation:

$$\equiv Si-Cl + ROH \rightleftharpoons \equiv SiOR + HCl$$

Therefore, to drive the reaction to favor high yields of the (β-cyanoalkyl)organooxysilane it is desirable to remove the hydrogen chloride as it is formed from the reaction mixture. In addition the hydrogen chloride liberated during the reaction can attack the starting materials and products to produce undesirable by-products which also lowers the yield of the desired products. For example, liberated hydrogen chloride can react with alcohol to produce a hydrocarbon chloride and water. This results in the loss of considerable alcohol. Furthermore, water formed by this side reaction can hydrolyze the chlorosilane producing undesirable polysiloxanes and generating more hydrogen chloride. In addition to these side reaction, those skilled in the art recognize that hydrogen chloride in combination with alcohol can readily convert cyanoalkyl radicals to carbalkoxyalkyl radicals. As a result there also can be produced during the organooxylation of β-cyanoalkylchlorosilanes up to 10 mole percent or more of the corresponding carbalkoxyalkylalkoxysilane. A build-up in this ester concentration can make the (β-cyanoalkyl)organooxysilane unsuitable as an intermediate for various applications. Removal of such esters from (β-cyanoalkyl)organooxysilane products by standard methods is difficult since the ester has a similar boiling point.

Therefore, it is an objective of the present invention to provide a process where hydrogen chloride liberated during the process is rapidly and effectively removed from the reaction mixture. The present inventors have found that this objective can be achieved by running the described equilibrium reaction in a thin-film process. The present process provides an effective means for removing reaction-liberated hydrogen chloride from the process and thereby shifting the chemical equilibrium of the process to favor production of (β-cyanoalkyl)organooxysilanes and also a means for minimizing side reactions and undesired by-products as a result of these side reactions. It is furthermore an objective of the present invention to provide a process with improved mass transfer thereby allowing for more efficient reactor operation than is achieved with reactive-distillation type reactors in which the reaction is typically conducted on a commercial scale.

Schubert, U.S. Pat. No. 3,008,975, issued Nov. 14, 1961, describes a stirred-batch process for alkoxylating chlorosilanes with an alcohol. The chlorosilanes can have a cyano-substituted monovalent hydrocarbon radical substituent. The process is run at pressures below about 200 mm Hg to improve yields of product and reduce by-product formation.

Nitzsche et al., U.S. Pat. No. 3,792,071, issued Feb. 12, 1974, describe an improved continuous process for producing alkoxysilanes in a reactive distillation process where the alcohol reactant is introduced into the column below the introduction point of the halosilane reactant. Temperature in the column is maintained above the boiling point of the alcohol and the product is removed below the point of introduction of the alcohol. Nitzsche et al. teach that the halosilane can be substituted with a β-cyanoethyl radical.

Schinabeck et al., U.S. Pat. No. 4,298,753, issued Nov. 3, 1981, describe a continuous two-stage process for preparing alkoxysilanes. The process comprises introducing in a liquid phase a chlorosilane and a hydroxyl-containing aliphatic compound in parallel flow into a first reactor; then removing the liquid reaction mixture from the first reactor and introducing it at the head of a column used as the second reactor, which is maintained at an elevated temperature, and adding a hydroxyl-containing aliphatic compound as a gas at the lower end of the column. An alkoxysilane product is recovered from the bottom of the column. Schinabeck et al. teach the chlorosilane may be substituted with a β-cyanoethyl radical.

Fischer et al., U.S. Pat. No. 4,506,087, issued Mar. 19, 1985, teach a continuous process for preparation of alkoxysilanes with hydrogen chloride contents of less than 20 ppm. In the described method, the esterification is performed in a reaction vessel and the raw esterification product is continuously removed and delivered to the top of a column. In the column, the reactant alcohol is vaporized and condensed at the top. The raw product drips from the top of the column to the bottom where it is collected. Fischer et al. teach that 2-cyanoethyltrichlorosilane can be a suitable starting compound for their process.

Bank et al., U.S. Pat. No. 4,924,022, issued May 8, 1990, teach a continuous system for the manufacture of organoalkoxysilanes. The reactor consists of a fractionating column that allows for completion of the reaction and separation of the hydrogen chloride formed as a by-product. Bank et al. teach cyanoethyltrimethoxysilane as an example of a product of the reactor.

SUMMARY OF INVENTION

The present invention is a process for the organooxylation of β-cyanoalkylchlorosilanes. The process comprises contacting in a film a β-cyanoalkylchlorosilane with an alcohol capable of forming an ester with the silicon of the β-cyanoalkylchlorosilane and thereby forming an equilibrium mixture comprising a (β-cyanoalkyl)organooxysilane and hydrogen chloride.

The thin film is heated at a temperature sufficient to cause vaporization of the hydrogen chloride from the equilibrium mixture thereby increasing yield of (β-cyanoalkyl)organooxysilane in the equilibrium mixture. In a preferred process, the process is run in a falling-film type reactor or a wiped-film type reactor.

DESCRIPTION OF INVENTION

The present invention is a process for organooxylation of β-cyanoalkylchlorosilanes. The process comprises:

(A) contacting in a film a β-cyanoalkylchlorosilane described by formula

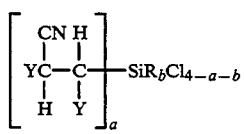

(1)

with an alcohol capable of effecting esterification with the silicon atom of the β-cyanoalkylchlorosilane thereby forming a (β-cyanoalkyl)organooxysilane and hydrogen chloride, (B) vaporizing the hydrogen chloride from the film to facilitate formation of the (β-cyanoalkyl)organooxysilane, and (C) recovering the (β-cyanoalkyl)organooxysilane; where each R is independently selected from a group consisting of hydrogen and substituted or unsubstituted monovalent hydrocarbon radical comprising one to about 12 carbon atoms, each Y is independently selected from a group consisting of hydrogen and alkyl radicals comprising one to about 12 carbons atom, a=1, 2, or 3, b=0, 1, or 2, and a+b=1, 2, or 3.

Beta-cyanoalkylchlorosilanes useful in the present process are described by formula (1). The esterification reaction of the present process requires that the β-cyanoalkylchlorosilane have at least one chlorine substituent on the silicon atom and as many as three chlorine substituent may be present on the silicon atom.

The β-cyanoalkylchlorosilane can have zero, one, or two substituents R, where each R is independently selected from a group consisting of hydrogen and substituted or unsubstituted monovalent hydrocarbon radical comprising one to about 12 carbon atoms. In addition to hydrogen, R may be for example alkyls such as methyl, ethyl, propyl, butyl, isobutyl, sec-butyl, octyl and 2-ethylhexyl; alkenyls such as vinyl and allyl; hexadienyls; cycloalkyls such as cyclopentyl, cyclohexyl, and cycloheptyl; aromatic hydrocarbon radicals such as phenyl and naphthyl; aralkyls such as benzyl and phenylethyl; alkaryls such as tolyl and dimethylphenyl; and substituted hydrocarbon radicals such as chloromethyl, 3-chloropropyl, and 3,3,3-trifluoropropyl.

The β-cyanoalkylchlorosilane described in formula (1) must contain at least one β-cyanoalkyl radical and can contain as many as three independently selected β-cyanoalkyl radicals. The β-cyanoalkyl radicals contain substituents Y where each substituent Y is independently selected from a group consisting of hydrogen and alkyl radicals comprising one to about 12 carbon atoms. Preferred is when each substituent Y is selected from a group consisting of hydrogen and methyl.

Examples of β-cyanoalkylchlorosilanes useful in the present process and methods for their making are described, for example, in Bank, U.S. Pat. No. 5,103,033, issued Apr. 7, 1992; Bank, U.S. Pat. No. 5,126,468, issued Jun. 30, 1992; and Bank, U.S. Pat. No. 5,126,469, issued Jun. 30, 1992, all of which are incorporated herein by reference.

A preferred β-cyanoalkylchlorosilane for use in the present process is selected from a group consisting of β-cyanoethylmethyldichlorosilane and β-cyanoethyltrichlorosilane.

The β-cyanoalkychlorosilane is contacted with an alcohol capable of effecting esterification with the silicon atom of the β-cyanoalkychlorosilane to form a (β-cyanoalkyl)organooxysilane and hydrogen chloride.

The process is not limited to the use of any particular aliphatic alcohol. Any alcohol which under the conditions of the present process is capable of effecting esterification with the silicon atom of the β-cyanoalkylchlorosilane is suitable. The only limitations imposed in the selection of an alcohol is the practical considerations of the boiling point of the alcohol, that it should contain only one hydroxyl group bonded directly to carbon, and that it should be devoid of other groups which are capable of interfering with the reaction. Therefore, those alcohols most effective in the present process contain only carbon, hydrogen, and oxygen, only one hydroxyl group bonded only to a non-carboxyl containing carbon atom, and any other oxygen in the alcohol is an ether group or part of an oxide or ester structure.

Suitable alcohols may include, for example, methanol, ethanol, n-propanol, isopropanol, n-butanol, isobutanol, tertiary butyl alcohol, n-pentanol, isopentanol, n-hexanol, 2-ethyl-n-hexanol, allyl alcohol, cyclohexanol, phenol, benzyl alcohol, 2-methoxyethanol, 2-ethoxyethanol, and 2-butoxyethanol.

Preferred is when the alcohol is a primary alkanol comprising about one to 12 carbon atoms. Most preferred is when the alcohol is selected from a group consisting of methanol and ethanol.

The molar ratio of alcohol to β-cyanoalkylchlorosilane used in the process will depend upon the number of silicon-bonded chlorine atoms and the number of such chlorine atoms on each silicon that are desired to be replaced with an organooxy group.

In general when it is desired to replace all of the chlorine atoms bonded to silicon, the molar ratio of alcohol to β-cyanoalkylchlorosilane can be varied within a range of about 60 to 140 percent of stoichiometric equivalence. However, it is preferred that the molar ratio of alcohol to β-cyanoalkylchlorosilane be within a range of about 95 to 110 percent of stoichiometric equivalence. Most preferred is when the molar ratio of alcohol to β-cyanoalkylchlorosilane is within a range of about 100 to 105 percent of stoichiometric equivalence. Stoichiometric equivalence herein is defined as one mole of alcohol per mole of silicon-bonded chlorine added to the process as β-cyanoalkylchlorosilane.

The alcohol and β-cyanoalkylchlorosilane are contacted in a film. In the present process, either the alcohol or the β-cyanoalkylchlorosilane or both must be in the liquid phase. However, those skilled in the art will appreciate that to form the film only one of the reactants need be in the liquid phase and the other can be contacted with the film as a vapor. Therefore, the alcohol, the β-cyanoalkylchlorosilane, or both may be preheated prior to contact as long as the above condition of at least one of the reactants being in a liquid phase is met. In a preferred process a film of the β-cyanoalkychlorosilane is formed and the alcohol is contacted with the film as a vapor.

The method of forming the film is not critical to the present process and can be any of those known in the art. The benefit of the present process is realized by the efficient mass transfer characteristics of the film allowing for a rapid vaporization and removal of hydrogen chloride from the film. The vaporization and removal of hydrogen chloride from the film results in a shift of the chemical equilibrium of the reaction to favor production of (β-cyanoalkyl)organooxysilanes and minimizes undesired side reactions as previously described.

The film can be formed, for example, in a falling film evaporator-type apparatus or in a wiped film evaporator-type apparatus. Examples of such apparatus are described, for example, in Kirk-Othmer, *Encyclopedia of Chemical Technology*, Fourth Edition, Vol. 9, p. 965–968, (1984); and in Mehra, "Selecting Evaporators," *Chemical Engineering*, Feb. 3, 1986, p. 56–72. The film forming apparatus employed as a reactor in the present process may be connected to a reboiler. The reactor may be used as a multiple-pass reactor, where materials exiting the reactor are recycled to the reactor to effect further reaction of the materials. Materials exiting the reactor may be fed to one or more similar reactors in series to effect further reaction. Product from the reactor or series of reactors may act as feed to other processes for further reacting and purifying the product, for example, distillation or reactive distillation processes.

Film thickness and flow rates will depend upon such factors as minimum wetting rate for the surface on which the film is formed and the flooding point for the film. Standard methods for determining these parameters are described, for example, in Perry et al., *Perry's Chemical Engineers' Handbook*, 6th Ed., McGraw-Hill, N.Y., p. 5-59, (1984); and in York et al., *Chemical Engineering Progress*, October, 1992, p. 93–98. The term "film" is meant to include the coating or spreading of a bulk liquid onto a surface so as to increase the surface area of the bulk liquid and thereby increase mass transfer of components from the liquid to a vapor phase.

Hydrogen chloride formed as the result of the contact of the alcohol with the β-cyanoalkylchlorosilane is vaporized from the film. Vaporization of the hydrogen chloride is effected by heating the film, by reducing pressure over the film, or by a combination of both. It is preferred that vaporization of the hydrogen chloride from the film be effected by heating the film. The film can be heated by standard methods, for example, passing a heated media such as a gas, water, or silicone oil through a jacket contacting a wall supporting the film. The film can be heated by heating one of the feed materials to the process above its vaporization point and contacting the vapor with the film. For example, the alcohol can be heated above its vaporization point and fed to a reactor counter current to the flow of a film of the liquid β-cyanoalkychlorosilane. Generally, it is preferred that the temperature of the film be as great as possible without effecting significant vaporization of the film. For example, when the film is β-cyanoethyltrichlorosilane or β-cyanoethylmethyldichlorosilane a useful temperature of the film is within a range of about 65° C. to 170° C.

An inert solvent may be used in the present process. The solvent may serve, for example, as a refluxing aid, diluent, carrier, or heating means in the present process. Generally, any inert solvent which does not enter into the reaction nor adversely affect the rate of reaction can be used. Preferred are those inert solvents which are liquid under normal conditions and have a boiling point below about 150° C. Examples of such solvents include hydrocarbon solvents such as toluene, xylene, pentane, hexane, nonane, and butane and chlorinated hydrocarbons exemplified by carbon tetrachloride, chloroform, methylene chloride, dichloroethane, dichloroethylene, 1,1,1-trichloroethane, trichloroethylene, perchloroethylene, and tetrachloroethane.

The hydrogen chloride vaporized from the present process is removed from the reactor by standard methods, for example venting, and can be collected and used as a feed to other processes. The hydrogen chloride vapor can be contacted, for example, with methyl chloride to effect cooling and removal of residual chlorosilanes and alcohol.

(β-Cyanoalkyl)organooxysilanes are recovered from the present process. The (β-cyanoalkyl)organooxysilanes which can be recovered from the present process are described by reference to formula (1), where one or more of the chlorine substituents of the silicon atom of the β-cyanoalkylchlorosilane is replaced by an organooxy radical. Preferred (β-cyanoalkyl)organooxysilanes prepared by the present process are those where in formula (1) R is methyl, a is one, b is zero or one, and all of the chlorine atoms bonded to the silicon atom are replaced by organooxy radicals.

The (β-cyanoalkyl)organooxysilane can be, for example, (β-cyanoethyl)trimethoxysilane, (β-cyanoethyl)methyldimethoxysilane, (β-cyanoethyl)triethoxysilane, (β-cyanoethyl)triphenoxysilane, bis-(β-cyanoethyl)dimethoxysilane, tris-(β-cyanoethyl)methoxysilane, (β-cyanoethyl)ethyldimethoxysilane, (β-cyanopropyl)trimethoxysilane, (β-cyanoethyl)phenyldimethoxysilane, (β-cyanoethyl)cyclohexyldimethoxysilane, (α-ethyl-β-cyanoethyl)methyldimethoxysilane, and (β-cyanoethyl)vinyldimethoxysilane.

Recovery of the (β-cyanoalkyl)organooxysilane from the present process may consist of simply retaining a (β-cyanoalkyl)organooxysilane containing liquid mixture resulting from the contact of the alcohol with the β-cyanoalkylchlorosilane in a film. Recovery of the (β-cyanoalkyl)organooxysilane can consist of using the (β-cyanoalkyl)organooxysilane containing liquid mixture as a feed, for example, to a reactive distillation column to effect further reaction of the mixture. Recovery of the (β-cyanoalkyl)organooxysilane can consist of standard separation processes, such as distillation, to further isolate the (β-cyanoalkyl)organooxysilanes.

The following examples are provided to illustrate the present invention. The examples are not intended to limited the scope of the claims.

Example 1

The methoxylation of cyanoethyltrichlorosilane in a falling-film type reactor was evaluated using three different configurations of process apparatus. The falling film reactor comprised a 5 cm outside diameter (O.D.) glass tube 23 cm in length. Located in the top end of the reactor was a distributor plate having positioned around the circumference 16 holes that were approximately 1 mm in diameter. In the center of the distributor plate was a 2.5 cm diameter hole with a 1.9 cm weir. Equally spaced below the distributor plate, to increase surface area within the reactor, were 5 doughnut-shaped rings having outside diameters of about 5.0 cm and inside diameters of about 2.5 cm. Below the distributor plate, the outside of the reactor was wrapped with heating tape for supplying heat to the reactor. The top of the reactor was connected to a dry ice condenser.

In Run 1 the bottom of the reactor was connected to a five bulb steam-heated condenser positioned on top of a reboiler. The reboiler was charged with 156.1 g of toluene which was heated to 104° C. A mixture of 189.1 g of cyanoethyltrichlorosilane and 142.7 g of toluene was pumped to a mixing tee at a rate of 6.96 mL/min. and methanol was pumped to the mixing tee at a rate of 2.6 mL/min. The resulting mixture was pumped to the top of the falling-film type reactor at a position located about 1.3 cm above the distributor plate. The walls of the reactor were maintained at a temperature within a range of 60° C. to 85° C. At the end of one hour the content of the reboiler was analyzed by gas liquid chromatography using a flame ionization detector (GLC-FID) and the results are reported in Table 1 as the area percent under the GLC-FID curve for each of the detected components. The chlorine content of the material recovered from the reboiler was determined by BCP titration and is reported in Table 1 as a weight percent under the heading "BCP % Chloride."

In Run 2 the bottom of the reactor was connected to an unheated 2.5 cm O.D. by 15 cm in length vigreaux column which was positioned on top of a reboiler. The reboiler was charged with 156.0 g of toluene which was heated to 112° C. A mixture of 246.5 g of cyanoethyltrichlorosilane and 203.5 g of toluene was pumped to the mixing tee at a rate of 6.62 mL/min. and methanol was pumped to the mixing tee at a rate of 2.55 mL/min. The resulting mixture was pumped to the top of the falling-film type reactor as previous described. The walls of the reactor were maintained at a temperature within a range of 80° C. to 85° C. At the end of one hour the content of the reboiler was analyzed by GLC-FID and by BCP titration as previously described. The results are reported in Table 1.

In Run 3 the bottom of the falling-film type reactor was connected directly to a reboiler. No heat was applied by the heating tape to the reactor. The reboiler was charged with 159.0 g of toluene which was heated to 112° C. A mixture of 245.0 g of cyanoethyltrichlorosilane and 203.5 g of toluene was pumped to the mixing tee at a rate of 6.93 mL/min. and methanol was pumped to the mixing tee at a rate of 2.50 mL/min. The resulting mixture was pumped to the top of the reactor as previous described. At the end of one hour the content of the reboiler was analyzed by GLC-FID and by BCP titration as previously described. The results are reported in Table 1.

TABLE 1

Methoxylation of Beta-Cyanoethyltrichlorosilane in a Falling-Film Type Reactor

|  | Run 1 | Run 2 | Run 3 |
|---|---|---|---|
|  | GLC-FID Area Percent | | |
| Methanol | 0.16 | 0.03 | 0.03 |
| Toluene | 83.70 | 80.20 | 79.20 |
| Cyanoethyltrimethoxysilane | 13.20 | 18.70 | 19.20 |
| —COMe ester | 0.22 | 0.08 | 0.06 |
|  | BCP % Chloride | | |
| % Chloride | 2.19 | 2.56 | 2.14 |

Example 2

The methoxylation of cyanoethyltrichlorosilane in a wiped-film type reactor was evaluated in a series of runs. The wiped-film type reactor comprised a 7.6 cm inside diameter (I.D.) by 25 cm length glass tube. Positioned 5 cm from the top of the reactor were three teflon wipe blades 15 cm in length which were held against the reactor wall by centrifugal action. The outside of the reactor had a heating jacket positioned 10 cm below the top of the reactor and ending 4 cm from the bottom. Thermocouples for temperature determination were positioned in the free volume of the reactor above and below the level of the heating jacket. Heat was provided to the heating jacket by steam at atmospheric pressure. The top of the reactor was connected to a dry ice condenser. The bottom of the reactor was connected to a reboiler. Methanol was vaporized and fed to the reactor through a port located above the reboiler and below the blades of the reactor. During each run product was continuously collected from the reboiler at a rate equal to the filling rate so as to maintain a constant volume in the reboiler.

In Run 4 the reboiler was charged with 153.0 g of xylene which was heated to 112° C. A mixture of 520.0 g of cyanoethyltrichlorosilane and 431.0 g of xylene was fed to the top of the reactor and vaporized methanol was fed to the reactor through the bottom port at 104% to 105% stoichiometric equivalence. The upper void temperature of the reactor was maintained at 22° C. and the lower void temperature at 90° C. during the run. At the end of two hours a sample was taken from the reboiler and analyzed by GLC-FID and by BCP titration as described in Example 1. The results are provided in Table 2.

In Run 5 the reboiler was charged with 151.7 g of xylene which was heated to 130° C. A mixture of 522.0 g of cyanoethyltrichlorosilane and 434.0 g of xylene was fed to the top of the reactor and vaporized methanol was fed to the reactor through the bottom port at 97% to 103% stoichiometric equivalence. The upper void temperature of the reactor was maintained at 25° C. and the lower void temperature at 90° C. during the run. At the end of two hours, a sample was taken from the reboiler and analyzed by GLC-FID and by BCP titration as described in Example 1. The results are provided in Table 2.

In Run 6 the reboiler was charged with 150.0 g of xylene which was heated to 110° C. to 120° C. during the run. A mixture of 524.0 g of cyanoethyltrichlorosilane and 434.0 g xylene was fed to the top of the reactor and vaporized methanol was fed to the reactor through the bottom port at 98% to 106% of stoichiometric equivalence. The upper void temperature of the reactor was maintained at 65° C. and the lower void temperature at 90° C. during the course of the run. At the end of two hours, a sample was taken from the reboiler and analyzed by GLC-FID and by BCP titration as described in Example 1. The results are provided in Table 2.

TABLE 2

Methoxylation of Beta-Cyanoethyltrichlorosilane in a Wiped-Film Type Reactor

|  | Run 4 | Run 5 | Run 6 |
|---|---|---|---|
|  | GLC-FID Area Percent | | |
| Methanol | 0.65 | 0.27 | 0.01 |
| Xylene | 65.00 | 73.40 | 75.86 |
| Cyanoethyltrimethoxysilane | 32.30 | 24.25 | 21.10 |
| —COMe ester | 0.10 | 0.03 | 0.02 |
|  | BCP % Chloride | | |

TABLE 2-continued

Methoxylation of Beta-Cyanoethyltrichlorosilane in a Wiped-Film Type Reactor

|  | Run 4 | Run 5 | Run 6 |
|---|---|---|---|
| % Chloride | 1.56 | 1.98 | 2.01 |

Example 3

The product from Run 6 in Example 2 was collected and fed a second pass through the wiped-film type reactor as described in Example 2. The reboiler connected to the reactor was washed with methanol and then charged with 150.0 g of xylene which was heated to 115° C. The product from Run 6, Example 2, was fed to the reactor at a rate of 10 mL/min. and vaporized methanol was fed through the bottom port at a rate of 0.35 mL/min. to 0.59 mL/min. At completion of addition of the product from Run 6, a sample was taken from the reboiler and analyzed by GLC-FID and by BCP titration as described in Example 1. The results are reported in Table 3.

TABLE 3

Second-Pass Methoxylation of Beta-Cyanoethyltrichlorosilane in a Wiped-Film Type Reactor

|  | Run 7 |
|---|---|
|  | GLC-FID Area Percent |
| Methanol | 0.02 |
| Xylene | 79.24 |
| Cyanoethyltrimethoxysilane | 19.67 |
| —COMe ester | 0.17 |
|  | BCP % Chloride |
| % Chloride | 0.16 |

Example 4

The methoxylation of cyanoethylmethyldichlorosilane in a wiped-film type reactor in the absence of solvent was evaluated. The reactor was the same as described in Example 2. The reboiler connected to the reactor was charged with 150 g of cyanoethylmethyldimethoxysilane which was heated to 100° C. Pressure in the reactor was reduced to about 190 mm of Hg. Cyanoethylmethyldimethoxysilane was fed to the top of the reactor at 3.33 mL/min. and methanol was fed as a vapor through the bottom port at about 1.71 mL/min. The upper void temperature of the reactor was maintained at 25° C. and the lower void temperature at 95° C. during the run. Product was collected from the reboiler for two hours as described in Example 2. After two hours of reactor run, a product sample was taken from the reboiler and analyzed by GLC-FID and by BCP titration as described in Example 1 and Example 3. The results are provided in Table 4.

TABLE 4

Methoxylation of Beta-Cyanoethylmethyldichlorosilane in a Wiped-Film Type Reactor

|  | Run 8 |
|---|---|
|  | GLC-FID Area Percent |
| Methanol | 0.02 |
| Cyanoethylmethyldimethoxysilane | 90.70 |
| —COMe ester | 2.20 |
|  | BCP % Chloride |
| % Chloride | 2.94 |

Example 5

The ethoxylation of cyanoethyltrichlorosilane in a wiped-film type reactor was evaluated. The reactor was the same as described in Example 2. The reboiler connected to the reactor was charged with 150 g of xylene which was heated to 120° C. A mixture comprising 523.7 g of cyanoethyltrichlorosilane and 434 g of xylene was fed to the top of the reactor and a 1.2% stoichiometric excess of ethanol was fed as a vapor to the bottom of the reactor. The upper void temperature of the reactor was maintained at about 75° C. and the lower void temperature at about 102° C. Product was collected from the reboiler for two hours and then a sample taken from the reboiler and analyzed by GLC-FID and by BCP titration as described in Example 1. The Results are provided in Table 4.

TABLE 4

Ethoxylation of Beta-cyanoethyltrichlorosilane in a Wiped-Film Type Reactor

|  | Run 9 |
|---|---|
|  | GLC-FID Area Percent |
| Ethanol | 0.3 |
| Cyanoethyltrimethoxysilane | 34.4 |
| Xylene | 63.1 |
| —COMe ester | 0.0 |
|  | BCP % Chloride |
| % Chloride | 0.64–1.70 |

We claim:

1. A process for organooxylation of cyanoalkylchlorosilanes, the process comprising:
   (A) contacting in a film a β-cyanoalkylchlorosilane described by formula

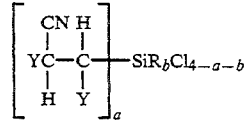

with an alcohol capable of effecting esterification with the silicon atom of the β-cyanoalkylchlorosilane thereby forming a (β-cyanoalkyl)organooxysilane and hydrogen chloride,
   (B) vaporizing the hydrogen chloride from the film to facilitate formation of the (β-cyanoalkyl)organooxysilane, and
   (C) recovering the (β-cyanoalkyl)organooxysilane; where each R is independently selected from a group consisting of hydrogen and substituted or unsubstituted monovalent hydrocarbon radical comprising one to about 12 carbon atoms, each Y is independently selected from a group consisting of hydrogen and alkyl radicals comprising one to about 12 carbons atoms, a=1, 2, or 3, b=0, 1, or 2, and a+b=1, 2, or 3.

2. A process according to claim 1, where each Y is independently selected from a group consisting of hydrogen and methyl.

3. A process according to claim 1, where the β-cyanoalkylchlorosilane is selected from a group consisting of β-cyanoethylmethyldichlorosilane and β-cyanoethyltrichlorosilane.

4. A process according to claim 1, where the alcohol is a primary alkanol comprising about one to 12 carbon atoms.

5. A process according to claim 1, where the alcohol is selected from a group consisting of methanol and ethanol.

6. A process according to claim 1, where the molar ratio of the alcohol to β-cyanoalkylchlorosilane is within a range of about 60 to 140 percent of stoichiometric equivalence.

7. A process according to claim 1, where the molar ratio of the alcohol to β-cyanoalkylchlorosilane is within a range of about 95 to 110 percent of stoichiometric equivalence.

8. A process according to claim 1, where the molar ratio of the alcohol to β-cyanoalkylchlorosilane is within a range of about 100 to 105 percent of stoichiometric equivalence.

9. A process according to claim 1, where a film of the β-cyanoalkylchlorosilane is formed and the alcohol is vaporized and contacted with the film.

10. A process according to claim 1, where the film is formed in a falling film evaporator-type apparatus.

11. A process according to claim 1, where the film is formed in a wiped film evaporator-type apparatus.

12. A process according to claim 1, where the vaporizing of the hydrogen chloride from the film is effected by heating the film.

13. A process according to claim 1, where the film is β-cyanoethyltrichlorosilane and the temperature of the film is within a range of about 65° C. to 170° C.

14. A process according to claim 1, where the thin is β-cyanoethylmethyldichlorosilane and the temperature of the film is within a range of about 65° C. to 170° C.

15. A process according to claim 1, where R is methyl, a=1, b=0 or 1, and all of the chlorine atoms bonded to the silicon atom of the β-cyanoalkylchlorosilane are replaced by organooxy radicals.

16. A process according to claim 15, where each Y is independently selected from a group consisting of hydrogen and methyl, the alcohol is selected from a group consisting of methanol and ethanol, the molar ratio of the alcohol to β-cyanoalkylchlorosilane is within a range of about 100 to 105 percent of stoichiometric equivalence, and a film of the β-cyanoalkylchlorosilane is formed and the alcohol is vaporized and contacted with the film.

* * * * *